United States Patent [19]

Böger et al.

[11] Patent Number: 4,515,798
[45] Date of Patent: May 7, 1985

[54] BENZOYLPARABANIC ACIDS

[75] Inventors: Manfred Böger, Weil am Rhein, Fed. Rep. of Germany; Jozef Drabek, Oberwil, Switzerland

[73] Assignee: Ciba Geigy Corporation, Ardsley, N.Y.

[21] Appl. No.: 507,257

[22] Filed: Jun. 23, 1983

[30] Foreign Application Priority Data

Jun. 25, 1982 [CH] Switzerland ............................ 3924/82
May 26, 1983 [CH] Switzerland ............................ 2870/83

[51] Int. Cl.³ .................... C07D 401/12; A61K 31/44
[52] U.S. Cl. .................................... 514/341; 546/278
[58] Field of Search .......................... 546/278; 424/263

[56] References Cited

U.S. PATENT DOCUMENTS 4,099,007 7/1978 Kraft et al. ........................... 546/278
4,212,869 7/1980 Carson et al. ........................ 546/278

*Primary Examiner*—Jane T. Fan
*Attorney, Agent, or Firm*—Edward McC. Roberts; Frederick H. Rabin

[57] ABSTRACT

Novel substituted 1-pyridyloxyphenyl-3-benzoylparabanic acids of the formula

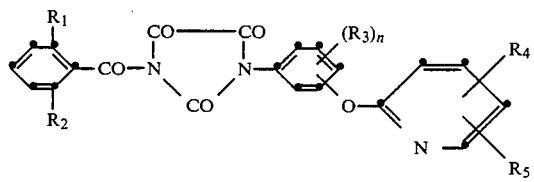

wherein $R_1$ is hydrogen, halogen or $C_1$–$C_4$alkyl, $R_2$ and $R_3$, each independently of the other, are halogen or $C_1$–$C_4$alkyl, $R_4$ is hydrogen or halogen, $R_5$ is halogen or $C_1$–$C_4$alkyl which is halogenated by fluorine and/or chlorine, and n is 0, 1 or 2, and the pyridyloxy group is linked to the phenyl group in the 3- or 4-position.

A process for the preparation of these compounds and compositions containing them for use in pest control, especially for controlling insects which attack plants and animals, are disclosed. The novel compounds are particularly effective against plant-destructive insects, especially when employed as ovicides.

16 Claims, No Drawings

BENZOYLPARABANIC ACIDS

The present invention relates to novel substituted 1-pyridyloxyphenyl-3-benzoylparabanic acids, to the preparation thereof, and to a method of use thereof in pest control.

The 1-pyridyloxyphenyl-3-benzoylparabanic acids have the formula I

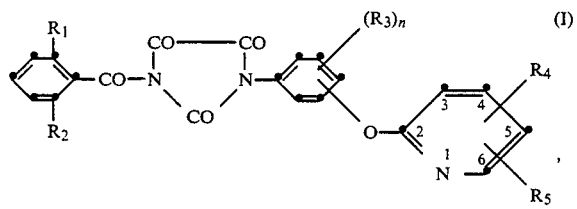

wherein $R_1$ is hydrogen, halogen or $C_1$-$C_4$alkyl; $R_2$ and $R_3$, each independently of the other, are halogens or $C_1$-$C_4$alkyl; $R_4$ is hydrogen or halogen; $R_5$ is halogen or $C_1$-$C_4$alkyl which is halogenated by fluorine and/or chlorine; and n is 0, 1 or 2, and the pyridyloxy group is linked to the phenyl group in the 3- or 4-position.

Preferred compounds of formula I are those, wherein $R_1$ is hydrogen, fluorine, chlorine, bromine or methyl; each of $R_2$ and $R_3$ independently of the other is fluorine, chlorine, bromine or methyl; $R_4$ is hydrogen or chlorine; and $R_5$ is chlorine or a methyl or ethyl group which is halogenated by fluorine and/or chlorine.

Compounds of formula I meriting special attention on account of their pesticidal activity are those, wherein $R_1$ is hydrogen, fluorine or chlorine, $R_2$ is fluorine, chlorine or methyl, $R_3$ is fluorine or chlorine; $R_4$ is hydrogen or chlorine in the 3- or 6-position of the pyridyloxy radical; and $R_5$ is a methyl or ethyl group which is perhalogenated by fluorine and/or chlorine.

Particularly interesting compounds of the formula I are also those wherein the radical $R_5$, which is preferably in the 5-position of the pyridyloxy radical, is —$CF_3$, —$CF_2CCl_3$, —$CF_2CFCl_2$ or —$CF_2CF_2Cl$. Preferred compounds of the formula I are also those wherein each of $R_1$ and $R_2$ independently of the other is fluorine or chlorine, but preferably both are fluorine. Particularly preferred compounds of the formula I are those werein $R_3$ is chlorine.

The compounds of formule I may be prepared by methods corresponding to known ones (cf. for example J. Agr. Food Chem. 21, No. 3, pp. 348-349, [1973], and a British patent specification No. 1 324 293).

For example, a compound of Formula I can be obtained by reacting a pyridyloxyphenylbenzoylurea of the formula II

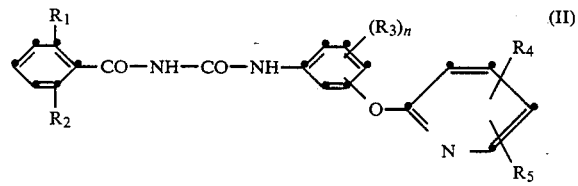

with oxalyl chloride. In formula II above, $R_1$ to $R_5$ and n are as defined for formula I.

The process of the invention can preferably be carried out under normal pressure and in the presence of an organic solvent or diluent. Examples of suitable solvets or diluents are: ethers and ethereal compounds such as dipropyl ether, dibutyl ether, dioxan, dimethoxyethane and tetrahydrofuran; N,N-dialkylated carboxamides; aliphatic, aromatic and preferably halogenated hydrocarbons, especially benzene, toluene, xylene, chloroform, methylene chloride, 1,2-dichloroethane, carbon tetrachloride and chlorobenzene; dimethylsulfoxide; and ketones, e.g. acetone, methyl ethyl ketone, methyl isopropyl ketone and methyl isobutyl ketone. The process is normally carried out in the temperature range from −10° to 200° C., preferably from 10° to 150° C., and most preferably at the boiling point of the solvent employed.

The starting materials of the formula II are known or they may be prepared by methods corresponding to known ones, e.g. as described in German Offenlegungsschrift No. 27 48 636.

Pesticidally active 1-phenyl-3-benzoylparabanic acids are known from British patent specification No. 1 324 293. In contradistinction thereto, the compounds of this invention are novel substituted 1-(2-pyridyloxyphenyl)-3-benzoylparabanic acids which, surprisingly, are more effective as pesticides, in particular as insecticides, in plant protection. A particular advantage of the compounds of formula I resides in their very low mammalian toxicity while being well tolerated by plants, along with advantageous solubility properties.

In particular, the compounds of the formula I are suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina, in particular mites and ticks.

In addition to their action against flies, e.g. *Musca domestica*, and mosquito larvae, the compounds of the formula I are also suitable for controlling plant-destructive feeding insects in ornamentals and crops of useful plants, especially in cotton (e.g. against *Spodoptera littoralis* and *Heliothis virescens*) and in fruit and vegetables (e.g. against *Laspeyresia pomonella, Leptinotarsa decemlineata* and *Epilachna varivestis*). The compounds of formula I have a pronounced ovicidal and larvicidal action against insects, especially against eggs and larvae of destructive feeding insects. When compounds of the formula I are ingested with the feed by adult insects, then reduced oviposition and/or a reduced hatching rate is observed in many pests, especially in Coleoptera, e.g. *Anthonomus grandis*.

Furthermore, the compounds of the formula I are suitable for controlling ectoparasites, such as *Lucilia sericata*, in domestic animals and productive livestock, e.g. by treating animals, cowsheds, barns, stables and pastures.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and *Bacillus thuringiensis* preparations.

Compounds of the formula I can also be combined with particular advantage with substances which exert a potentiating effect on pesticides. Examples of such compounds include: piperonyl butoxide, propynyl ethers, propynyl oximes, propynyl carbamates and propynyl phosphates, 2-(3,4-methylenedioxyphenoxy)-3,6,9-trioxaundecane or S,S,S-tributylphosphorotrithioate.

The good insecticidal activity of the compounds of formula I corresponds to a mortality rate of at least 50 to 60% of the insect pests referred to above.

The compounds of the formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethl or monoethyl ether, ketones, such as cyclohexanone, strongly polar solvents, such as N-methyl-2-pyrrolidone, dimethyl sulfoxide or dimethyl formamide, as well as epoxidised vegetable oils, such as epoxidised coconut oil or soybean oil; or water. The solid carriers used e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials, such as calcite or sand. In addition, a great number of pregranulated materials of inorganic or organic nature can be used, e.g. especially dolomite or pulverised plant residues.

Depending on the nature of the compound of the formula I, or of the combination of such compound with other insecticides or acaricides to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts, as well as of modified and non-modified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyoxyethylene adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "McCutcheon's Detergents and Emulsifiers Annual", MC Publishing Corp., Ringwood, N.J., 1981, and H. Stache, "Tensid-Taschenbuch", Carl Hanser Verlag, Munich/Vienna, 1981.

The pesticidal formulations usually contain 0.1 to 99%, preferably 0.1 to 95%, of a compound of the formula I or of a combination of a compound of formula I with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The formulations can also contain further additives, such as stabilisers, antifoams, viscosity regulators, binders, adhesives, as well as fertilisers, in order to produce special effects.

Formulation Examples for solid compounds of formula I or combinations thereof with other insecticides or acaricides (throughout, percentages are by weight)

| Wettable powders | (a) | (b) | (c) |
|---|---|---|---|
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 67% | 27% | — |

The active ingredient or combination is thoroughly mixed with the adjuvants and the mixture is thoroughly ground in a suitable mill, affording wettable powders which can be diluted with water to give suspensions of the desired concentration.

Emulsions of any required concentration can be obtained from this concentrate by dilution with water.

| Dusts | (a) | (b) |
|---|---|---|
| compound of formula I or combination | 5% | 8% |
| talcum | 95% | — |
| kaolin | — | 92% |

Ready for use dusts are obtained by mixing the active ingredient with the carriers, and grinding the mixture in a suitable mill.

| Extruder granulate | |
|---|---|
| compound of formula I or combination | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
|---|---|
| compound of formula I or combination | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 1

Preparation of 1-[4-(5-trifluoromethyl-2-pyridyloxy)phenyl]-3-(2,6-difluorobenzoyl)parabanic acid 12.6 g of N-4-(5-trifluoromethyl-2-pyridyloxy)phenyl-N-2,6-difluorobenzoylurea and 4.4 g of oxalyl chloride are dissolved in 100 ml of 1,2-dichlorethane and the solution is refluxed for 20 hours. The solvent is then distilled off and the residue is suspended in a mixture of toluene/hexane (1:1 parts by volume) and collected by filtration. Recrystallisation from toluene (80° C.) yields the title compound of the formula

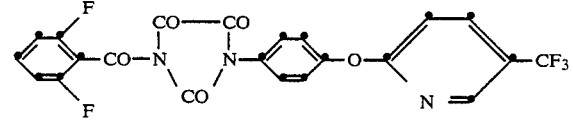

as a white crystalline powder with a melting point of 152°–154° C. (compound 1).

The following compounds of formula I are prepared in accordance with the procedure described in this Example:

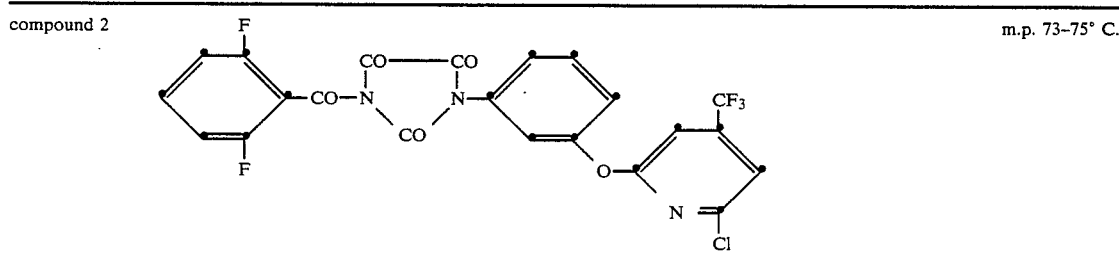

compound 2    m.p. 73–75° C.

| | | |
|---|---|---|
| compound 3 | 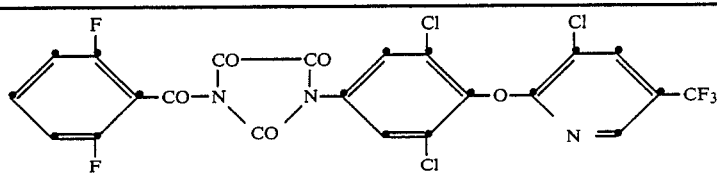 | m.p. 157–158° C. |
| compound 4 | 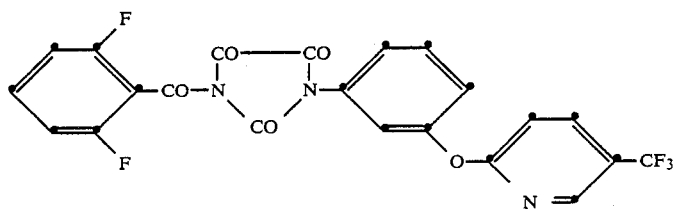 | m.p. 77–80° C. |
| compound 5 | 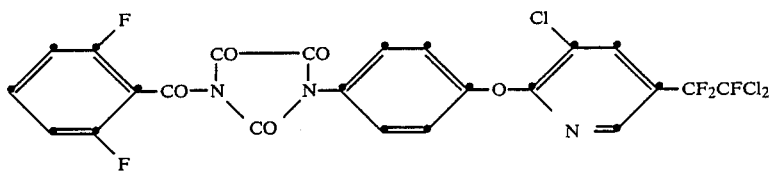 | m.p. 166–168° C. |
| compound 6 | 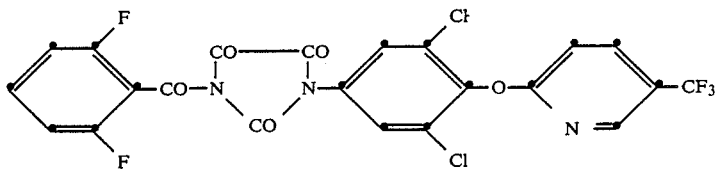 | m.p. 143–146° C. |
The following compounds of formula I are obtainable in corresponding manner:
| compound 7 | 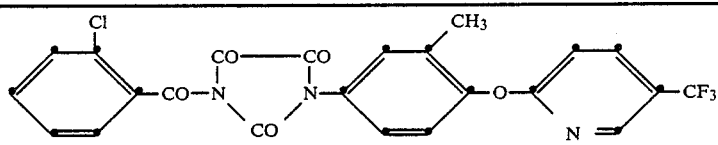 |
|---|---|
| compound 8 | 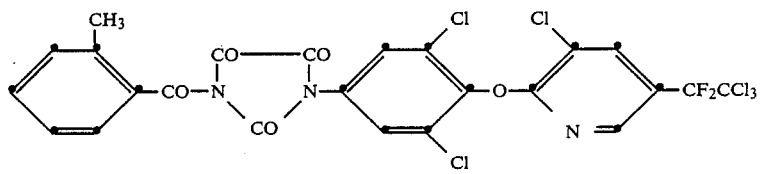 |
| compound 9 | 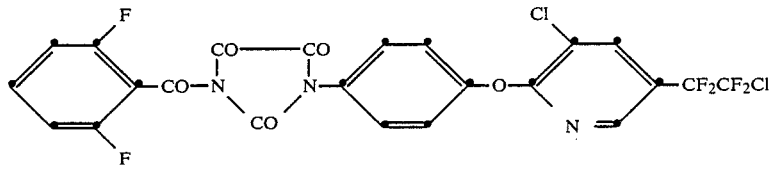 |
| compound 10 | 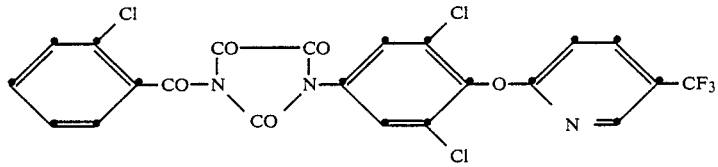 |
EXAMPLE 2
Action against *Musca domestica*
50 g of freshly prepared nutrient substrate for maggots are charged into beakers. A specific amount of a 1% acetonic solution of the respective test compound is pipetted into the nutrient substrate present in the beakers. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing, with each test compound at one of its given concentrations. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made 10 days later of the number of flies which have hatched out of the pupae.

The compounds of Example 1 are very effective in this test.

EXAMPLE 3

Action against *Lucilia sericata*

1 ml of an aqueous formulation containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate. Compounds of Example 1 are very effective in this test against *Lucilia sericata*.

EXAMPLE 4

Action against *Aedes aegypti*

Active ingredient concentrations of 800 and 400 ppm respectively are obtained by pipetting a specific amount of a 0.1% solution in acetone of each compound to be tested onto the surface of 150 ml of water in a beaker. After the acetone has evaporated, 30 to 40 two-day-old larvae of *Aedes aegypti* are put into each of the beakers containing the solution of test compound. Mortality counts are made after 1, 2 and 5 days.

Compounds of Example 1 are very effective in this test against *Aedes aegypti*.

EXAMPLE 5

Insecticidal stomach poison action

Potted cotton plants having a height of about 25 cm were sprayed with aqueous emulsions containing each compound to be tested in concentrations of 400, 200, 100, 50, 12.5 and 0.75 ppm. After the spray coating has dried, the cotton plants are populated with *Spodoptera littoralis* and *Heliothis virescens* larvae in the $L_3$-stage. The test is carried out at 24° C. and 60% relative humidity. The percentage mortality is determined after 120 hours.

The following test compounds effect 80 to 100% kill of *Spodoptera littoralis* larvae at the given concentrations: compound 2 at 12.5 ppm, compound 3 at 0.75 ppm, compound 4 at 200 ppm and compound 5 at 100 ppm.

The following test compounds effect 80 to 100% kill of *Heliothis virescens* larvae at the given concentrations: compound 2 at 50 ppm, compound 3 at 0.75 ppm and compounds 4 and 5 at 100 ppm.

EXAMPLE 6

Action against *Epilachna varivestis*

*Phaseolus vulgaris* plants (dwarf beans) about 15–20 cm in height are sprayed with aqueous emulsion formulations containing the compound to be tested in concentrations of 400 and 800 ppm. After the spray coating has dried, each plant is populated with 5 larvae of *Epilachna varivestis* (Mexican bean beetle) in the $L_4$-stage. A plastic cylinder is slipped over the treated plants and covered with a copper gauze top. The test is carried out at 28° C. and 60% relative humidity. The acute activity (percentage mortality) is assessed after 2 and 3 days. Evaluation of feeding damage (anti-feeding effect), and of inhibition of development and shedding, is made by observing the test organisms for a further 3 days.

The compounds of Example 1 are very effective in this test.

EXAMPLE 7

Ovicidal action against *Heliothis virescens*

Corresponding amounts of a wettable powder formulation containing 25% by weight of test compound are mixed with sufficient water to produce aqueous emulsions of increasing concentration. One-day-old egg deposits of Heliothis on cellophane are immersed in these emulsions for 3 minutes and then dried by suction on round filters. The treated deposits are placed in petri dishes and kept in the dark. The hatching rate in comparison with untreated controls is determined after 6 to 8 days. Evaluation is made by determining the minimum concentration necessary for 100% kill of the eggs.

The compounds of Example 1 are very effective in this test.

EXAMPLE 8

Action against *Laspeyresia pomonella* (eggs)

Egg deposits of *Laspeyresia pomonella* not more than 24 hours old are immersed, on filter paper, for 1 minute in acetonic aqueous solutions containing 12.5, 50, 100 and 400 ppm respectively of test compound. After the solution has dried, the eggs are placed in petri dishes and kept at a temperature of 28° C. The percentage of larvae hatched from the treated eggs is determined after 6 days.

Compound 1 of Example 1 effects 80 to 100% kill in this test at a concentration of 12.5 ppm. Compound 5 effects 80 to 100% kill at a concentration of 400 ppm.

EXAMPLE 9

Inhibition of reproduction of *Anthonomous grandis*

*Anthonomous grandis* adults which are are not more than 24 hours old after hatching are transferred in groups of 25 to barred cages. The cages are then immersed for 5 to 10 seconds in an acetonic solution containing 1.0% by weight of the compound to be tested. After the beetles have dried, they are put into covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae had developed from the eggs.

The duration of the inhibiting effect of the compounds to be tested on reproduction is determined by monitoring the egg deposits over a period of about 4 weeks. Evaluation is made by assessing the reproduction in the number of deposited eggs and hatched larvae in comparison with untreated controls.

The compounds of the formula I are very effective in this test.

EXAMPLE 10

Action against *Anthonomus grandis*

Two cotton plants in the 6-leaf stage, in pots, are sprayed with an aqueous wettable emulsion formulation containing 12.5, 50, 100 and 400 ppm of the compound to be tested. After the spray coating has dried (about 1½ hours), each plant is populated with 10 adult beetles (*Anthonomus grandis*). Plastic cylinders, the tops of which are covered with gauze, are placed over the plants populated with the beetles in order to prevent these latter from migrating. The plants were then kept at 5° C. and about 60% relative humidity. Evaluation is made after 2, 3, 4 and 5 days by determining the percentage mortality of the test insects (percentage in dorsal position) as well as the antifeeding action.

Compound of Example 1 effects 80 to 100% kill at 12.5 ppm in this test.

What is claimed is:

1. A compound of the formula I

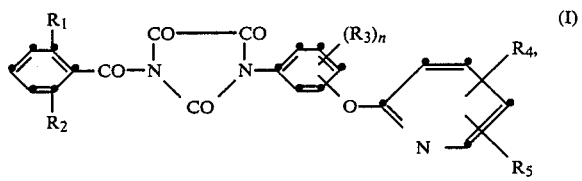

wherein $R_1$ is hydrogen, halogen or $C_1-C_4$alkyl; $R_2$ and $R_3$, each independently of the other, are halogen or $C_1-C_4$alkyl; $R_4$ is hydrogen or halogen; $R_5$ is halogen or $C_1-C_4$alkyl which is halogenated by fluorine and/or chlorine; and n is 0, 1 or 2; and the pyridyloxy group is linked to the phenyl group in the 3- or 4-position.

2. A compound of the formula I according to claim 1, wherein $R_1$ is hydrogen, fluorine, chlorine, bromine or methyl; each of $R_2$ and $R_3$ independently of the other is fluorine, chlorine, bromine or methyl; $R_4$ is hydrogen or chlorine; and $R_5$ is chlorine or a methyl or ethyl group which is halogenated by fluorine and/or chlorine.

3. A compound of the formula I according to claim 2, wherein $R_1$ is hydrogen, fluorine or chlorine; $R_2$ is fluorine, chlorine or methyl; $R_3$ is fluorine or chlorine; $R_4$ is hydrogen or chlorine in the 3- or 6-position of the pyridyloxy radical; and $R_5$ is a methyl or ethyl group which is perhalogenated by fluorine and/or chlorine.

4. A compound of the formula I according to claim 3, wherein $R_5$ is $-CF_3$, $-CF_2CCl_3$, $-CF_2CFCl_2$ or $-CF_2CF_2Cl$.

5. A compound of the formula I according to claim 1, wherein the radical $R_5$ is in the 5-position.

6. A compound of the formula I according of claim 1 wherein each of $R_1$ and $R_2$ independently of the other is fluorine or chlorine.

7. A compound of the formula I according to claim 6 wherein $R_1$ and $R_2$ are fluorine.

8. A compound of the formula I according to claim 1 wherein $R_3$ is chlorine.

9. A compound according to claim 7 of the formula

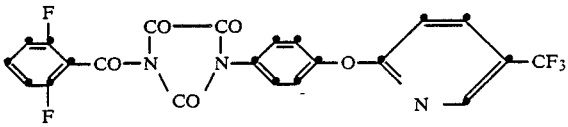

10. A compound according to claim 7 of the formula

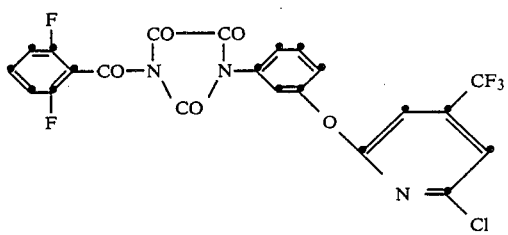

11. A compound according to claim 7 of the formula

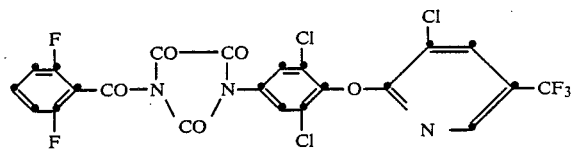

12. A compound according to claim 7 of the formula

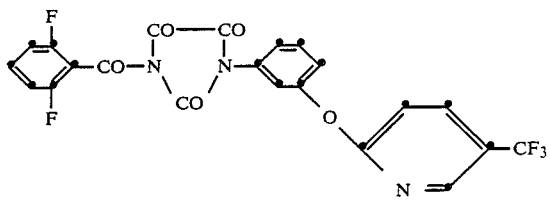

13. An insecticidal composition which contains, as active component, an insecticidally effective amount of a compound according to claim 1, together with suitable carriers and/or other adjuvants.

14. A method of controlling insects, which comprises applying to said insects or to the locus thereof a insecticidally effective amount of a compound as claimed in claim 1.

15. A method according to claim 14, wherein the insects to be controlled are plant-destructive feeding insects.

16. A method according to claim 15, wherein the compound is applied as ovicide.

* * * * *